US011330237B2

(12) United States Patent
Themelis (10) Patent No.: US 11,330,237 B2
(45) Date of Patent: May 10, 2022

(54) MEDICAL INSPECTION APPARATUS, SUCH AS A MICROSCOPE OR ENDOSCOPE USING PSEUDOCOLORS

(71) Applicant: LEICA INSTRUMENTS (SINGAPORE) PTE. LTD., Singapore (SG)

(72) Inventor: George Themelis, Lindau (DE)

(73) Assignee: LEICA INSTRUMENTS (SINGAPORE) PTE. LTD., Singapore (SG)

(*) Notice: Subject to any disclaimer, the term of this patent is extended or adjusted under 35 U.S.C. 154(b) by 0 days.

(21) Appl. No.: 17/062,595

(22) Filed: Oct. 4, 2020

(65) Prior Publication Data
US 2021/0021795 A1 Jan. 21, 2021

Related U.S. Application Data

(63) Continuation of application No. 15/424,819, filed on Feb. 4, 2017, now abandoned.

(30) Foreign Application Priority Data

Feb. 15, 2016 (EP) .................................. 16155625

(51) Int. Cl.
*H04N 9/43* (2006.01)
*A61B 1/00* (2006.01)
(Continued)

(52) U.S. Cl.
CPC ........... *H04N 9/43* (2013.01); *A61B 1/00009* (2013.01); *A61B 1/043* (2013.01); *A61B 5/0071* (2013.01);
(Continued)

(58) Field of Classification Search
CPC ...... H04N 9/43; H04N 9/646; A61B 1/00009; A61B 1/043; A61B 5/0071; A61B 5/7425;
(Continued)

(56) References Cited

U.S. PATENT DOCUMENTS

2005/0159662 A1* 7/2005 Imanishi .............. A61B 3/1025
600/473
2005/0203343 A1* 9/2005 Kang .................. A61B 1/00009
600/160

(Continued)

FOREIGN PATENT DOCUMENTS

| CN | 104299212 A | 1/2015 |
|----|-------------|--------|
| JP | 2003111716 A | 4/2003 |
| JP | 2003159210 A | 6/2003 |

OTHER PUBLICATIONS

Glatz, Jurgen et al. "Robust overlay schemes for the fusion of fluorescence and color channels in biological imaging"; Apr. 2014; Journal of Biomedical Optics (Year: 2014).*

(Continued)

*Primary Examiner* — Joseph G Ustaris
*Assistant Examiner* — Matthew David Kim
(74) *Attorney, Agent, or Firm* — Hodgson Russ LLP (57) ABSTRACT

The invention relates to a medical inspection apparatus (1), such as a microscope or endoscope, and to a medical inspection method such as microscopy or endoscopy. Visible image data (11) representing a visible-light image (49) and fluorescence image data (12) representing a fluorescent-light image (51) and a pseudocolor (70, 71) are merged to give an improved visual rendition of an object (2) which comprises at least one fluorophore (6) to mark special features of the object (2). This is accomplished in that an image processing unit (18) of the microscope (1) or endoscope is configured to compute a color ($r_o$, $g_o$, $b_o$) of an output pixel (54) in the (Continued)

pseudocolor image (53) from at least one pseudocolor ($r_p$, $g_p$, $b_p$), a color ($r_i$, $g_i$, $b_i$) of a first input pixel (50) in the visible-light image (49) and an intensity (f) of a second input pixel (52) in the fluorescent-light image (51). In particular, the color ($r_o$, $g_o$, $b_o$) may result from a linear interpolation in a color space (RGB) between the pseudocolor and the color of the first input pixel (50) of the visible-light image (49) depending on the intensity (f) of the second input pixel (52) in the fluorescent-light image.

17 Claims, 5 Drawing Sheets
(4 of 5 Drawing Sheet(s) Filed in Color)

(51) Int. Cl.
| | |
|---|---|
| *A61B 1/04* | (2006.01) |
| *A61B 5/00* | (2006.01) |
| *G02B 21/36* | (2006.01) |
| *G01N 21/64* | (2006.01) |
| *G06T 5/50* | (2006.01) |
| *G02B 21/00* | (2006.01) |
| *H04N 9/64* | (2006.01) |

(52) U.S. Cl.
CPC ....... *A61B 5/7425* (2013.01); *G01N 21/6458* (2013.01); *G02B 21/008* (2013.01); *G02B 21/0028* (2013.01); *G02B 21/0076* (2013.01); *G02B 21/367* (2013.01); *G06T 5/50* (2013.01); *H04N 9/646* (2013.01); *A61B 2576/00* (2013.01); *G06T 2207/10024* (2013.01); *G06T 2207/10056* (2013.01); *G06T 2207/10064* (2013.01); *G06T 2207/10068* (2013.01); *G06T 2207/20221* (2013.01)

(58) Field of Classification Search
CPC ............ G01N 21/6458; G02B 21/0028; G02B 21/0076; G02B 21/008; G02B 21/367; G06T 5/50
USPC .......................................................... 348/34
See application file for complete search history.

(56) References Cited

U.S. PATENT DOCUMENTS

| | | | |
|---|---|---|---|
| 2007/0203413 A1* | 8/2007 | Frangioni | ............ A61B 1/3132 |
| | | | 600/478 |
| 2008/0267490 A1 | 10/2008 | Gorges et al. | |
| 2009/0268010 A1 | 10/2009 | Zhao et al. | |
| 2011/0082369 A1 | 4/2011 | Mohr et al. | |
| 2011/0177003 A1 | 7/2011 | Shu et al. | |
| 2011/0205382 A1 | 8/2011 | Kanaris et al. | |
| 2011/0305405 A1 | 12/2011 | Kawamura | |
| 2012/0218394 A1 | 8/2012 | Yoshino et al. | |
| 2012/0328178 A1* | 12/2012 | Remiszewski | ....... A61B 5/7257 |
| | | | 382/133 |
| 2014/0296718 A1 | 10/2014 | Kishima | |
| 2016/0061654 A1 | 3/2016 | Corwin et al. | |
| 2016/0157722 A1 | 6/2016 | Kubo et al. | |
| 2016/0231170 A1 | 8/2016 | Wei | |
| 2017/0213344 A1 | 7/2017 | Hong et al. | |
| 2017/0370843 A1 | 12/2017 | Marcu et al. | |

OTHER PUBLICATIONS

Snyder, George L. "Response to Office Action dated Aug. 10, 2018 for U.S. Appl. No. 15/424,819"; dated Dec. 9, 2018; Hodgson Russ LLP (Year: 2018).*

Glatz, Jürgen, et al., Robust overlay schemes for the fusion of fluorescence and color channels in biological imaging, Journal of Biomedical Optics, vol. 19(4), Apr. 2014.

* cited by examiner

MEDICAL INSPECTION APPARATUS, SUCH AS A MICROSCOPE OR ENDOSCOPE USING PSEUDOCOLORS

CROSS REFERENCE TO RELATED APPLICATIONS

This application is a continuation of U.S. application Ser. No. 15/424,819 filed Feb. 4, 2017, and claims priority of European patent application number 16155625.3 filed Feb. 15, 2016, the entire disclosure of which is incorporated by reference herein.

FIELD OF THE INVENTION

The invention relates to a medical inspection apparatus, such as a microscope or endoscope, and to a medical inspection method such as a microscopy or endoscopy.

BACKGROUND OF THE INVENTION

Microscopes and endoscopes using fluorescence of fluorophores to better discern certain types of tissue are known. The present invention aims to improve the quality of the images displayed to a surgeon as compared to the existing microscopes or endoscopes.

SUMMARY OF THE INVENTION

For a medical inspection apparatus such as a microscope or endoscope, this objective is achieved in that the microscope or endoscope comprises an image processing unit, the image processing unit comprising a first input section configured to receive visible image data representing a visible-light image of an object, a second input section configured to receive fluorescence image data representing a fluorescent-light image of the object, and an output section configured to output pseudocolor image data representing a pseudocolor image of the object, wherein the image processing unit is adapted to compute a color of an output pixel in the pseudocolor image from at least one pseudocolor, a color of a first input pixel in the visible-light image and an intensity of a second input pixel in the fluorescent-light image.

The medical inspection method according to the invention comprises the steps of acquiring visible image data representing a visible-light image of an object, acquiring fluorescence image data representing a fluorescent-light image of the object, combining the visible-light image data, the fluorescence image data and at least one pseudocolor to obtain output data representing a pseudocolor image, wherein a color of an output pixel in the pseudocolor image depends on at least one pseudocolor, a color of a first input pixel in the visible-light image, and an intensity of a second input pixel in the fluorescent-light image.

Further, the object is solved by a non-transitory computer readable medium storing a program, causing a medical visualization apparatus to execute the above-cited method.

The solution according to the invention creates a pseudocolor image in which the at least one pseudocolor is blended in a natural-looking way into the visible-light image. Thus, the section of the object, which is colored by the fluorescent color, is presented in a more natural way. The fluorescent-light image is not simply overlaid onto the visible-light image, but is rather merged with the visible-light image using the at least one pseudocolor to display the fluorescent parts of the object.

The invention can be further improved by the following aspects, which are each advantageous on their own, and can be combined arbitrarily.

In as far as the terms "image" and "data" or operations upon images or data are mentioned in the following, it is to be understood that the terms "image" and "data" can be used synonymously, as the image represents the totality of the data making up the image. The data of an image may also be grouped into pixels. Thus, a "pixel" corresponds to an ordered grouping of the "data". The images and data are processed and/or stored digitally and are themselves digital.

The at least one pseudocolor need not correspond to the color of fluorescence of the fluorophore, but can be chosen by the user of the microscope or endoscope. Preferably, the pseudocolor is a color in the visible-light range which does not naturally occur in the object to be observed.

According to another aspect of the invention, the medical visualization apparatus is stereoscopic. In a stereoscopic microscope or endoscope, a separate pseudocolor image recorded from a slightly different point of view, is presented to each eye of the observer. Thus, in a stereoscopic microscope or endoscope, two separate pseudocolor images are computed from two different visible-light images and two fluorescent-light images. For each of the two stereoscopic channels, the same devices and processes may be used as for the single channel of a monocular microscope.

The fluorescent-light image may be sampled by a digital NIR camera, the visible-light image by a standard camera. The image processing unit may comprise a memory in which image data are stored. The image processing unit may be part of a general-purpose computer which has been adapted, e.g. by software, to provide a control and processing system for a microscope or endoscope. It is also possible that the image processing unit is a specially-designed electronic device that can be solely used in microscopes or endoscopes.

According to another aspect of the invention, the microscope or endoscope may comprise more than one fluorescent channel. For example, two or more fluorophores may be used which are each excited at different excitation wavelengths and which each emit fluorescent light at different emission wavelengths. Two or more fluorophores can be used to identify different aspects of the object under investigation. For example, one type of fluorophore can be used to mark blood vessels whereas another fluorophore may mark tumourous cells. Another fluorophore may be used to mark e.g. nerve cells.

According to one aspect of the invention, the fluorescence image data may contain at least two different fluorescent emission colors and the processing unit may be configured to assign a different pseudocolor to each of the different fluorescent emission colors. Thus, the different types of tissues marked by the different types of fluorophores can be discerned in the pseudocolor image by the different pseudocolors. According to the invention, the different pseudocolors are all blended naturally into the visible-light image due to the consideration of both the color of the first input pixel and the intensity of the second input pixel in the fluorescent-light image.

For the computation of the color of the output pixel, the first and second input pixel should correspond to the same feature of the object. For example, the fluorescent-light image, the visible-light image and the pseudocolor image may have the same size, i.e. comprise the same number of pixel rows and pixel columns. If the visible-light and fluorescent-light images are congruent to each other, i.e. the size, orientation and location of the object is the same in the two images, the first and second input pixel are located in the same row and column in their respective images.

To improve the blending, the color of the output pixel may be located linearly, in a color space, between the color of the first input pixel and the at least one pseudocolor, the distance between the color of the output pixel and the color of the first input pixel being proportional to the intensity of the second input pixel. Typical color spaces are HSV, HSI, RGB and YMCK without being limited to these color spaces. In the color space, each color can be represented by a positional vector. Thus, computing the color of the output pixel can be done, computationally efficient by vector arithmetics.

Using an RGB color space as an example, the image processing unit may be configured to linearly interpolate the RGB values of the first input pixel in the visible-light to the selected pseudocolor value dependent on the intensity of the second input pixel to obtain the color of the output pixel. Assuming that the first input pixel has RGB values $(r_i, g_i, b_i)$, and that the fluorescence intensity is f, an interpolation factor ($h=f/f_{max}$, where $f_{max}$ is the maximum expected fluorescence intensity) can be chosen. If the pseudocolor that has been selected by the user for a particular fluorophore has RGB values $(r_p, g_p, b_p)$, the color $(r_o, g_o, b_o)$ of the output pixel may be as follows:

$$r_o = r_i + h \cdot (r_p - r_i)$$

$$g_o = g_i + h \cdot (g_p - g_i)$$

$$b_o = b_i + h \cdot (b_p - b_i).$$

Thus, if the fluorescence intensity is f=0, then h=0 and the color of the output pixel will correspond to the color of the visible-light image. The more intense the pixel in the fluorescent-light image is, the closer the color of the output pixel will be to the pseudocolor.

In the above equation, the factor h may be replaced with a factor $k=a \cdot h$, where a is a pseudocolor opaqueness factor which determines how opaque the pseudocolor is in the pseudocolor image. The pseudo-color opaqueness factor a may be selected by the user. Setting the opaqueness factor e.g. to very small values below 1 will lead to a very weak pseudocolor in the pseudocolor image, even if $f=f_{max}$.

To improve the quality of the pseudocolor image and to avoid noise artifacts, the processing unit may comprise a threshold adjustment module, which is configured to blank a pixel in the fluorescence image if that pixel has an intensity below a threshold value. The threshold value may be adjustable by a user and stored in a memory section of the image processing unit. In operation of the medical visualization apparatus, pixels in the fluorescent-light image having an intensity lower than $f_{min}$ are set to zero. The threshold filter eliminates dark noise and crosstalk. Using the threshold filter or the threshold adjustment module, respectively, modifies the factor h which becomes $$h=0 \text{ for } f < f_{min},$$

and $$h=f \text{ for } f > f_{min}.$$

Furthermore, the image processing unit may comprise a gamma correction module which is adapted to apply a gamma correction to at least one of the fluorescence image data and the visible image data. In particular, the gamma correction is applied to the fluorescent-light data in order to make the fluorescent-light image appear to be a black-and-white fluorescent-light image.

According to another aspect of the invention, the processing unit may comprise a homogenization module, which is configured to compensate at least one of vignetting and inhomogeneous illumination in at least one of the visible image data and the fluorescence image data. For example, the homogenization module may apply a flat-field filter to the visible image data and/or the fluorescence image data.

Inhomogeneities in illumination and vignetting of the imaging optics result in uneven brightness across the field of view. Typically, the periphery of the field of view is significantly darker in microscopes or endoscopes than the center and therefore only the central part of the field of view is typically usable for digital imaging in microscopy or endoscopy. However, the surgeon can still observe visually, via the eyepieces of the microscope or endoscope, the whole field of view. Thus, there can be a mismatch of the fields of view as used in the pseudocolor image on one hand, and as observed by the surgeon on the other hand. To avoid this mismatch, a digital homogenization filter may be applied to the visible image data and/or the fluorescence image data. The homogenization filter is adapted to correct the inhomogeneities in illumination and/or vignetting by the imaging optics. After application of the homogenization filter, the resulting intermediate image has the same brightness throughout the whole field of view. In the homogenization filter, the working distance, the focal length of the microscope or endoscope optics, the focus and the illumination intensity settings may all be considered.

In particular, the homogenization filter may be obtained by calibration, e.g. by using as the object a uniformly colored, e.g. grey or white, target from which a calibration image is obtained. The uniform white target reveals both vignetting and illumination inhomogeneities.

The homogenization filter may be determined from the calibration image by measuring the RGB values preferably separately along a spatial profile in the visible-light image and/or fluorescent-light image. The spatial profile may be e.g. a diagonal or any other straight line through the center of the calibration image. The spatial profiles may be fitted with a polynomial and may be rotated around the center of the image to create a 2-dimensional inhomogeneity map which, by inversion, results in the homogenization filter.

The homogenization filter may be stored in a memory section of the image processing unit. The homogenization module may comprise different homogenization filters for the visible image data and for the fluorescence image data to account for different optics and illumination in the visible-light image on one hand, and of the fluorescent-light image on the other hand.

If the visible-light image is recorded by a different camera than the fluorescent-light image, two different viewing angles or alignment errors may occur for the visible-light and the fluorescent-light images. The fluorescent-light image and the visible-light image may thus not exactly be congruent to each other. For example, the visible-light image may be slightly rotated with respect to the fluorescent-light image. Also, the fluorescent-light image may be shifted with respect to the visible-light image. Finally, the visible-light image and the fluorescent-light image may be anamorphic with respect to each other.

Thus, in order to blend the visible-light image and the fluorescent-light image naturally into each other, it is advantageous if the processing unit comprises a spatial adjustment module, which is adapted to bring the visible-light image and the fluorescent-light image into congruence to each other. The spatial adjustment module ensures that the first input pixel and the second input pixel map the same spot on the object. In particular, the spatial adjustment module may be adapted to at least one of crop, rotate, shift and stretch at least one of the visible-light image and the fluorescent-light image.

If more than one fluorescence channel is used, a separate camera for each fluorescent emission color may be used. If a single camera for recording a fluorescent-light image comprising more than one fluorescence emission color is used, it is preferred that a color-sensitive camera or recording method is used to be able to distinguish the different fluorescence bands from each other. Band-pass filters may be used, which band-pass filters only let pass the emission wavelengths of the different fluorophores.

Although several aspects of the microscope or endoscope have been described above with reference to modules of the image processing unit, it is possible that these modules are, at least partly, functional units incorporated in software executed by the image processing unit. Cumulatively or alternatively, the modules may also be at least partly represented in hardware.

In the following, exemplary embodiments of the invention are described with reference to the drawings. As explained above, the combination of features shown in these embodiments can be changed according to the needs of the specific application. For example, if, in a specific application, the technical effect of a particular feature of the embodiment shown is not needed, this feature can be omitted. Conversely, if, for a specific embodiment, the technical effect of one of the above-described features is needed, this feature may be added to the shown embodiment.

BRIEF DESCRIPTION OF THE DRAWING VIEWS

The patent or application file contains at least one drawing executed in color. Copies of this patent or patent application publication with color drawing(s) will be provided by the Office upon request and payment of the necessary fee.

Throughout the drawings, the same reference numerals are used for elements which correspond to each other in at least one of their structure and function.

In the drawings.

DETAILED DESCRIPTION OF THE INVENTION

Figure 1:
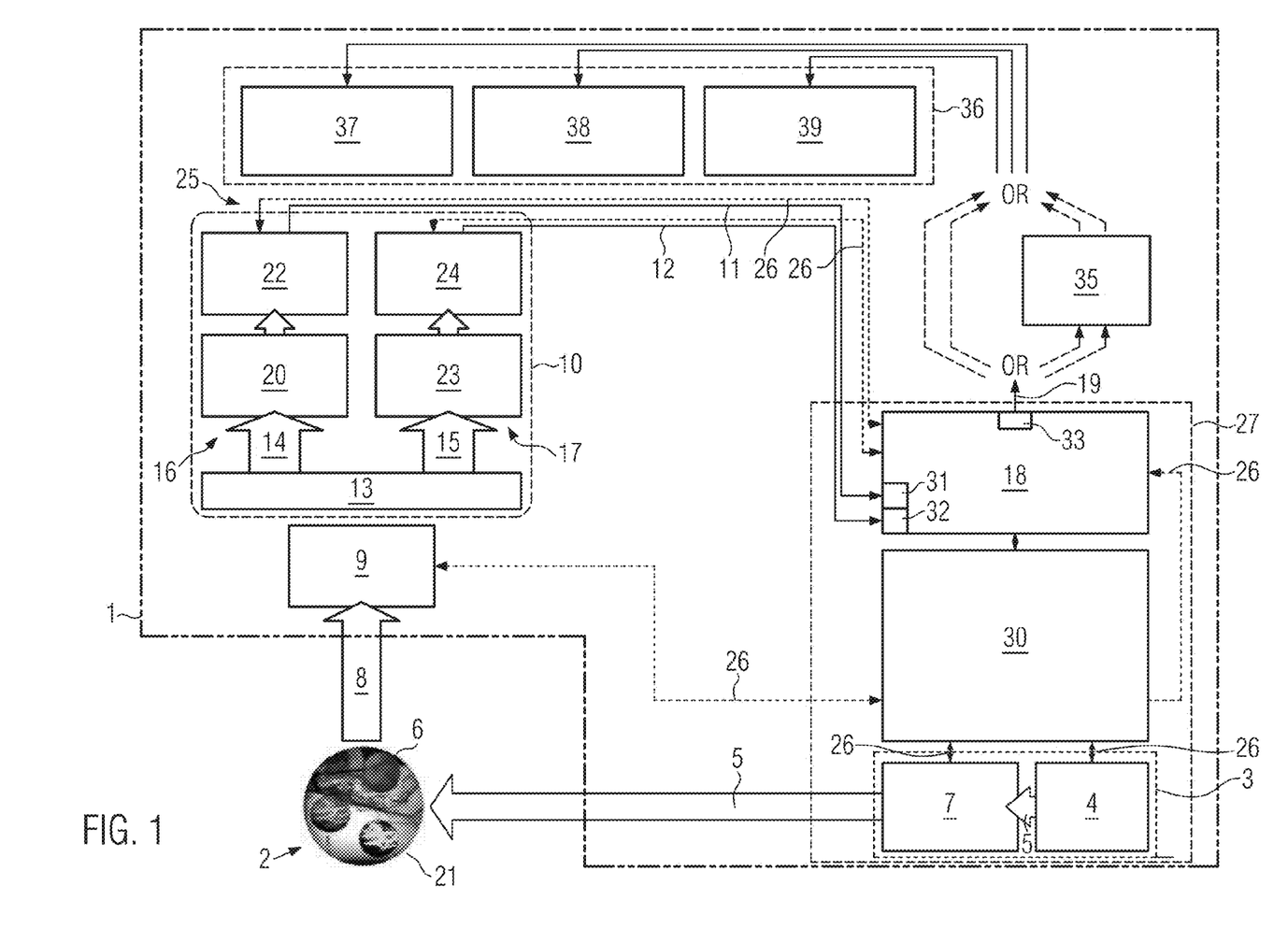
FIG. 1 shows a schematic representation of a medical visualization apparatus according to the invention.

First, the general structure of a medical inspection apparatus 1 according to the invention is described with reference to FIG. 1. In FIG. 1, the medical inspection apparatus 1 is shown as a microscope solely for explanatory purposes.

The microscope 1 is used to visually inspect an object 2, such as tissue of a body of a human or animal e.g. for preparing for surgery or during surgery. For this, the object 2 is illuminated by a lighting subsystem 3 comprising at least one light source 4. The light 5 from the light source 4 may be transmitted through the object 2 or be reflected by the object 2. A fluorophore 6, i.e. a fluorescent fluid, solid, or suspension, may be present in the object 2. The light source may emit light 5 containing energy in a band of wavelength, which excites the fluorescence of the at least one fluorophore 6.

The lighting subsystem 3 may comprise one or more illumination filters 7 through which the light 5 from the at least one light source 4 is directed. For example, the illumination filters 7 may comprise a band-pass filter, which allows light to pass only in the excitation band of the at least one fluorophore and in the visible-light range. In particular, the at least one illumination filter 7 may block any light from the light source 4 at those wavelengths, at which the at least one fluorophore emits fluorescent light.

Additionally or alternatively, the illumination filters may also serve to homogenize the illumination, and may include apertures.

The light 8 reflected and/or emitted from the object 2 is received by an optical subsystem 9, such as a magnifying zoom lens.

The light from the optical subsystem 9 is passed to an imaging subsystem 10, which is adapted to extract visible image data 11 and fluorescence image data 12 in the form of electric signals, from the light 8 reflected and/or emitted from the object 2 and any fluorescent material at or in the object 2.

The visible image data 11 are representative of a visible-light image of the object 2, i.e. a digital image which corresponds to what can be seen by the eyes of a human observer. The fluorescence image data 12 are representative of a fluorescent-light image. The fluorescent-light image corresponds to a digital image of the object in the emission wavelengths of the at least one fluorophore 6 in the object 2.

In order to be able to use the full spectrum of visible light in the visible image data 11, it is preferred that both the excitation band and the emission band for the at least one fluorophore is not in the visible light range. For example, both the emission band and the excitation band can be in the near infrared (NIR). Suitable fluorophores may be 5-aminolevulinic acid which, in a metabolism, results in protoporphyrin IX, which is fluorescent, and indocyanine green.

The imaging subsystem 10 comprises a dichoroic or polychroic beam splitter 13 which separates the incoming light 8 into visible light 14 and NIR light 15, the latter containing both the excitation wavelengths reflected by the object 2 and the emitted wavelengths from the at least one fluorophore in the object 2. The imaging subsystem 10 contains a visible-light imaging assembly 16 and a fluorescent-light imaging assembly 17 in which the visible light 14 and NIR light 15 are treated differently, both optically and on the signal level, until the visible image data 11 and the fluorescence image data 12 are combined in an image processing unit 18 of the microscope 1 to a pseudocolor image, which is represented by output data 19 available at the image processing unit 18.

In the visible-light imaging assembly 16, one or more visible observation filters 20 may be arranged which block all but the visible light. Further, the visible observation filter 20 may comprise an optical homogenization filter for rendering the intensity in the field of view 21 observed by the optical subsystem 8 more homogeneous. The visible light 14 is recorded by a visible-light camera 22 and converted to the visible image data 11.

To obtain the fluorescence image data 12, the NIR light 15 is filtered by a fluorescence observation filter 23 and then directed to a fluorescence camera 24, which may be an NIR camera. The fluorescence observation filter 23 may be configured as a band-pass filter which blocks all but the light in the emission wavelengths of the at least one fluorophore 6. Thus, the NIR camera 24 records images containing information only in the emission wavelengths. The NIR camera may be a black-and-white camera or may be color-sensitive. The latter is particularly useful if more than one fluorophore used as the excitation wavelengths of the various fluorophores can be discerned by their different color in the fluorescent-light image. In this case, the fluorescence observation filter may be a multiple band-pass filter for allowing the different fluorescence wavelengths through.

The imaging subsystem 10 may comprise a data interface 25, which makes the visible image data 11 from the visible-light camera 22 and the fluorescence image data 12 from the fluorescence camera 24 available to other subsystems of the microscope 1.

The imaging subsystem 10 operates in real-time by providing the visible image data 11 and the fluorescence image data 12 with no or almost no delay as compared to the optical image received by the optical subsystem 9.

The data interface 25 of the imaging subsystem 10 may provide the visible image data 11 and the fluorescence image data 12 in a standard data format for a video stream. Further, the data interface 25 of the fluorescent imaging subsystem 10 may be configured to receive control signals 26 e.g. to control camera settings. Furthermore, the imaging subsystem may be configured to change settings of at least one of the visible observation filter 20 and the fluorescence observation filter 23, if at least one of the visible observation filter 20 and the fluorescence observation filter 23 is adjustable.

The microscope 1 may be a stereoscopic microscope. In this case, an imaging subsystem 10 may be present for each stereoscopic channel.

In the embodiment of FIG. 1, a control and processing subsystem 27 is connected for one- or bi-directional data transfer to the fluorescent imaging subsystem 10 e.g. to receive in operation the visible image data 11 and the fluorescence image data 12 and to exchange control signals 26.

Further, the control and processing subsystem 27 may be configured to control the optical subsystem 9 via control signals 26 and/or the lighting subsystem 3, also via control signals 26. If the illumination filters are adjustable, the control and the processing subsystem 27 may be configured to also control the illumination filters 7.

Control and processing subsystem 27 may be a general-purpose computer, such as a personal computer, or a dedicated electronic system which has been specifically adapted to the requirements of the microscope 1. The data transfer between the various subsystem, assemblies and other devices of the microscope 1 may be facilitated if a digital communication bus is used.

The control and processing subsystem 27 may comprise several units that may be realized in hardware and/or software.

For example, a controller unit 30 may be used to store, alter, and control the setting of operative parameters of the microscope 1. The operational parameters may include but not be limited to parameters of the optical subsystem 9, such as an aperture, focus and focal length, parameters of the lighting subsystem 3 such as illumination filter settings, brightness of the light source, parameters of the fluorescent imaging subsystem 10, such as camera settings and settings of the observation filters, and parameters of the image processing unit 18. The controller unit 30 may comprise elements for user interaction which, upon operation, change the operational parameters. Such elements may include a graphical user interface on a screen or a touchscreen, and/or mechanical elements such as sliders, push buttons, switches and/or knobs.

The image processing unit 18 comprises a first input section 31, which is configured to receive the visible image data 11. A second input section 32 of the image processing unit 18 is configured to receive the fluorescence image data 12. The output data 19 are provided at an output section 33 of the image processing unit 18.

At the output section 33, the output data 19 are available in the form of pseudocolor image data which represent a pseudocolor image of the object 2.

In the pseudocolor image, the visible-light image is merged with the fluorescent-light image providing smooth color transitions from the visible-light image to the fluorescent-light image, whereby the fluorescent-light image is assigned and displayed in a pseudocolor. The color of an output pixel in the pseudocolor image is computed by the image processing unit 18 from the at least one pseudocolor, a color of a first input pixel in the visible-light image and an intensity of a second input pixel in the fluorescent-light image. If more than one fluorophore is used, each fluorophore, or its fluorescence emitting waveband respectively, is assigned a different pseudocolor, preferably by the user, or automatically.

As can be further seen in FIG. 1, the microscope 1 may either be provided with or connected to a documentation subsystem 35 for storing both all or selective image data preferably together with the microscope settings. Further, the microscope 1 may comprise a monitoring subsystem 36 comprising preferably several displays, such as an eyepiece display 37 and microscope monitor 38. The microscope 1 may also be provided with a display interface 39 which is configured to supply video data to an external monitor (not shown).

Figure 2:
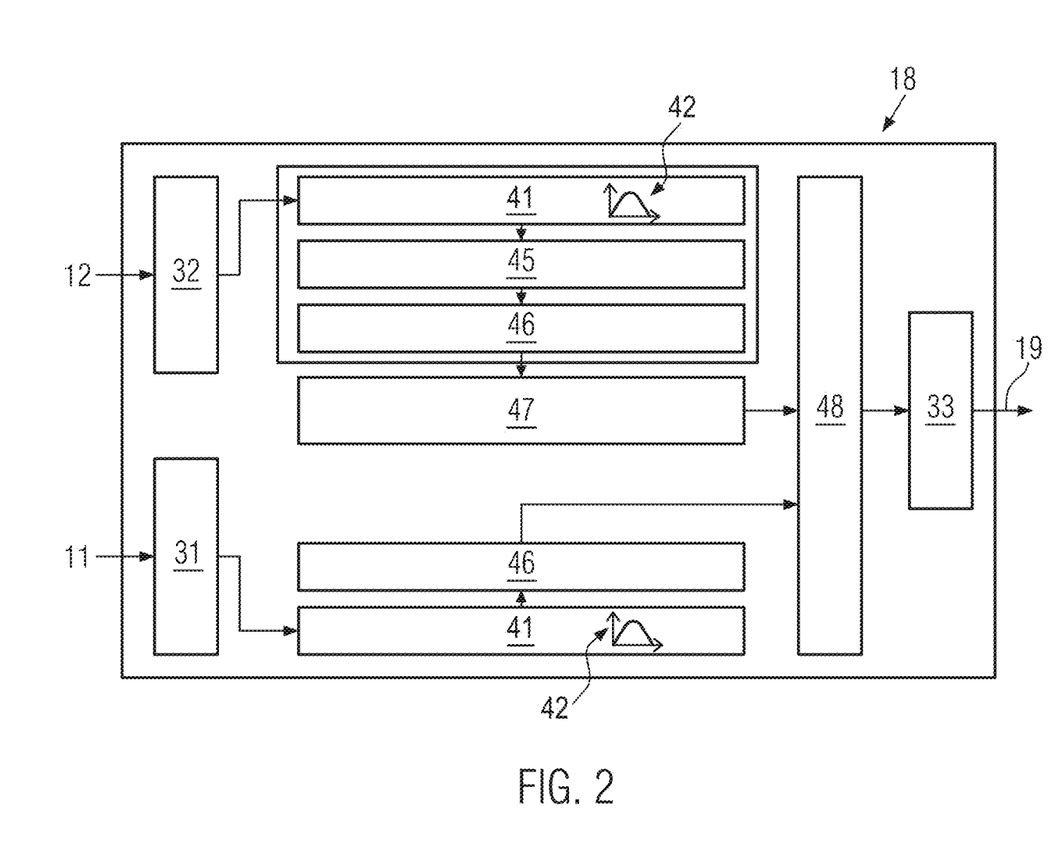
FIG. 2 shows a schematic representation of an image processing unit of a medical visualization apparatus according to the invention.

FIG. 2 shows schematically the structure of the image processing unit 18. The image processing unit 18 comprises a plurality of modules, which perform different image processing functions on the image data 11, 12 in real time. The modules of the image processing unit 18 may be implemented in hardware and/or software. Different modules which perform the same function may be e.g. be implemented as identical software routines which are fed with different data. The modules may be executed in parallel or sequentially provided that in a sequential execution, the output is still available in real time.

The image processing unit 18 may comprise a homogenization module 41 which is configured to compensate at least one of vignetting and inhomogeneous illumination in at least one of the visible image data 11 and the fluorescence image data 12. The homogenization module may be further configured to do a histogram normalization and optimization of the image data 12 in order to make full use of the contrast range of the image.

The homogenization module 41 may comprise a digital homogenization filter 42 which may be different for the visible image data 11 and the fluorescence image data 12 as the distribution of illumination may be different for visible light and light in the excitation band of the at least one fluorophore. Further, the cameras may exhibit different vignetting and distortion characteristics which makes an individual compensation necessary.

Figure 3A:
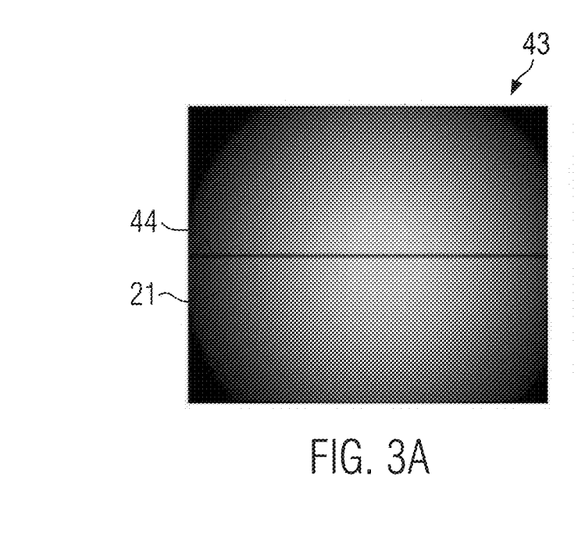
FIG. 3A shows a schematic representation of a homogeneously colored object to calibrate a homogenization filter.
Figure 3B:
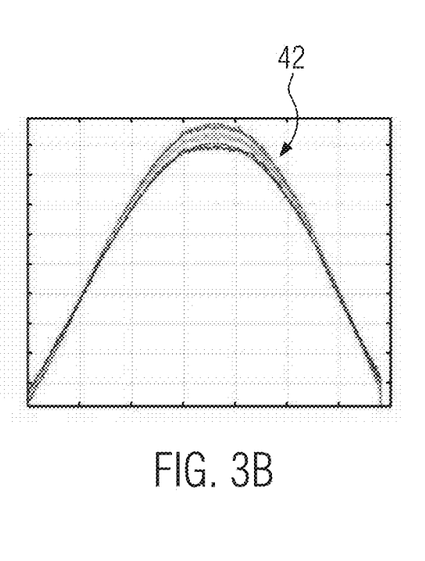
FIG. 3B shows a schematic representation of a homogenization filter.

The homogenization filter 42 may be determined using calibration for example of a homogeneously colored calibration object 43, such as a white, grey or otherwise uniformly colored plate and stored electronically in the image processing unit 18 or an attached memory. FIG. 3A shows an image of such a homogeneously colored calibration object 43. The inhomogeneous illumination and the vignetting are clearly visible in the image of the calibration object as the periphery of the field of view 21 is significantly darker than the center. In the homogenization module 41, a homogenization filter 42 as shown in FIG. 3B is applied in real time to at least one of the visual-light image and the fluorescent-light image. The homogenization filter 42 results from the RGB values along a spatial profile 44 from the image of the calibration object. For each coordinate in the color space, a separate profile is obtained. The different profiles may be fitted with polynomials. Rotating the polynomial curves around the center of the image creates a two-dimensional map of the inhomogeneities in the respective optical path between the object 2 and the sensor in the respective camera 22, 24. The homogenization filter 42 results from inverting the homogeneity map.

Further, the image processing unit 18 may comprise a spatial adjustment module 45 which preferably acts only on one of the fluorescence image data 12 and the visible image data 11, preferably the fluorescent data 12 only, as the fluorescence image data 12 may be less than the visible image data 11 due to a lower color depth. The spatial adjustment module 45 is adapted to at least one of crop, rotate, shift and stretch at least one of the visible-light image and the fluorescent-light image. The purpose of the spatial adjustment module 45 is to bring the visible-light image and the fluorescent-light image into congruence to each other, so that a pixel at a certain location in the visible image corresponds to the same spot on the object 2 as the pixel at the same location in the fluorescent-light image. In the spatial alignment module 45, correlation algorithms and pattern detection algorithms may be executed to match corresponding structures in the visible-light image and the fluorescent-light image and to compute the amount of cropping, shifting, stretching and/or rotating necessary to align the two images to each other.

Further, the image processing unit 18 may comprise a gamma correction module 46 which is configured to act on at least one of the visible image data 11 and the fluorescence image data 12. By using the gamma correction, the images can be adapted to human vision.

The image processing unit 18 may further comprise a threshold adjustment module 47 which is preferably configured to act on the fluorescence image data 12 only. The threshold adjustment module 47 is configured to blank a pixel in the fluorescence image data 12 if this pixel has an intensity f below a threshold value $f_{min}$: f=f, if f>$f_{min}$, and f=0, if f<$f_{min}$. The controller unit 30 (FIG. 1) may be configured to allow adjustment of the threshold value by a user.

Blanking a pixel comprises one of setting the color of the pixel to a pre-determined color, such as black, setting it to zero and making the pixel transparent.

Finally, the image processing unit 18 may comprise a pseudo color image generator 48, which is adapted to merge the visible-light image and the fluorescent-light image to generate the pseudocolor image available at the output section 33.

In the following, the function of the pseudocolor image generator 48 is described with reference to a color space, for example an RGB color space. In the RGB color space, a Cartesian coordinate system is formed by the three component colors red (r), green (g), and blue (b). Other color spaces which may be alternatively used may be the CMYK color space or the HSL or HSV color space.

In RGB color space, any color is represented by its components (r, g, b) and thus corresponds to a certain location in the 3-dimensional color space. This location corresponds to a position vector pointing from the origin of the color space to the specific color.

The pseudocolor image generator 48 is configured to linearly interpolate the color of an output pixel in the pseudocolor image from the pseudocolor to the color of the first input pixel in the visible-light image depending on the intensity of the second input pixel. Thus, in the color space, the color ($r_o$, $g_o$, $b_o$) of the output pixel is located linearly between the color ($r_i$, $g_i$, $b_i$) of the first input pixel in the visible-light image and the at least one pseudocolor ($r_p$, $g_p$, $b_p$) i.e. located on a vector pointing from ($r_i$, $g_i$, $b_i$) to ($r_p$, $g_p$, $b_p$). The distance between the color ($r_o$, $g_o$, $b_o$) of the output pixel and the color ($r_i$, $g_i$, $b_i$) of the first input pixel is computed to be proportional to the intensity f of the second input pixel in the fluorescent-light image. Thereby, both the first input pixel and the second input pixel correspond to the same spot on the object 2 (FIG. 1). Using the color space allows to do the linear interpolation using computationally efficient vector arithmetics.

In particular, the color ($r_o$, $g_o$, $b_o$) of the output pixel can be calculated in the pseudocolor image generator 48 as follows:

$$r_o = r_i + h \cdot (r_p - r_i)$$

$$g_o = g_i + h \cdot (g_p - g_i)$$

$$b_o = b_i + h \cdot (b_p - b_i),$$

where the factor h=f/$f_{max}$, $f_{max}$ being the maximum expected fluorescence intensity.

Thus, the intensity of the fluorescence in the second input pixel determines the distance between the output color and the input color for any given color component. If the fluorescence intensity f=0, i.e. there is no fluorescence, the color of the output pixel will correspond to the color of the first input pixel in the visible-light image. If the fluorescence in the second output pixel is maximum, f=$f_{max}$, the color of the output pixel will correspond to the pseudocolor ($r_p$, $g_p$, $b_p$).

In a further variant, an opaqueness factor a may be used in combination with the factor f/$f_{max}$ to form an alternative factor h=a·(f/$f_{max}$). The opaqueness factor a may be adjusted by the user upon interaction with the control and processing subsystem 27 to increase or decrease the transparency of the pseudocolor. If factor a is close to zero, even highly fluorescent parts of the fluorescent-light image will hardly be visible in the pseudocolor image. Increasing factor a will increase visibility of the pseudocolor The process of assigning a color ($r_o$, $g_o$, $b_o$) in the output data based on the intensity in the fluorescence image data and the color ($r_i$, $g_i$, $b_i$) of a corresponding pixel in the visible image data is exemplarily shown in FIG. 4, where green is used as pseudo color ($r_p$, $g_p$, $b_p$)=(0,256,0), for example. The upper square represents a (schematic) visible light image 49 with 4×4 first input pixels 50. Only for explanatory purposes, the sample visible-light image 49 contains only four colors which are identical throughout every column in the visible-light image.

Figure 4:
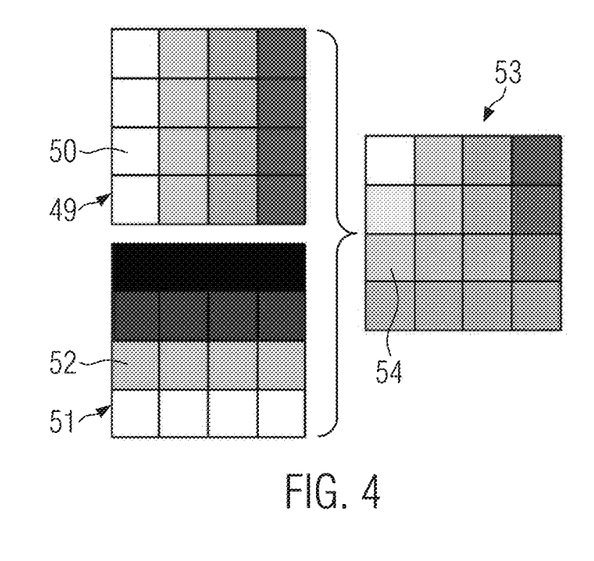
FIG. 4 shows a schematic representation of the effects of image processing on image data.

The lower square on the left-hand side shows schematically the intensity in a sample 4×4 fluorescent-light image 51. The fluorescent-light image consists of 4×4 second input pixels 52. Only for explanatory purposes, the intensity in each row of the fluorescent-light image 51 is constant. The upmost row of second input pixels 52 has zero intensity, whereas the lowest row of second input pixels 52 in the fluorescent-light image 51 has maximum intensity.

Using the above linear RGB interpolation scheme, a 4×4 pseudocolor image 53 results. Again, it can be seen that, if the intensity of the second input pixel 52 is zero, the original color in the visible-light image 49 is reproduced in the corresponding output pixel 54 of pseudocolor image 53. If the intensity of the second input pixel 52 is maximum, the color in the pseudocolor image 53 depends on the opaqueness factor a as explained above.

In FIG. 4, the different steps for merging the visible-light image 49 and a fluorescent-light image 51 to obtain a pseudocolor image 53 are shown.

In a first step 60, the visible-light image 49 and the fluorescent-light image 51 are sampled by the visible-light camera 22 and the fluorescent-light camera 24, respectively. In a second step 61, the respective images 49, 51 are homogenized using the homogenization module.

In a third step 62, the homogenized fluorescent-light image 51 is brought into congruence with the visible-light image so that the physical structures in the two images 49, 51 correspond to each other both in size and location. The spatial adjustment is preferably done before the fluorescent-light image 51 is worked upon by the threshold adjustment module 47, so that the algorithms for the spatial adjustment have more data available for pattern matching.

In a fourth step 63, a threshold-filtering of the fluorescent-light image 51 takes place to blank all second input pixels 52 in the fluorescent-light image 51 which are below the intensity threshold $f_{min}$.

In a fifth step 64, the pseudocolor image 53 is computed using the pseudocolor image generator 48 with the above-described linear color interpolation.

Figure 5:
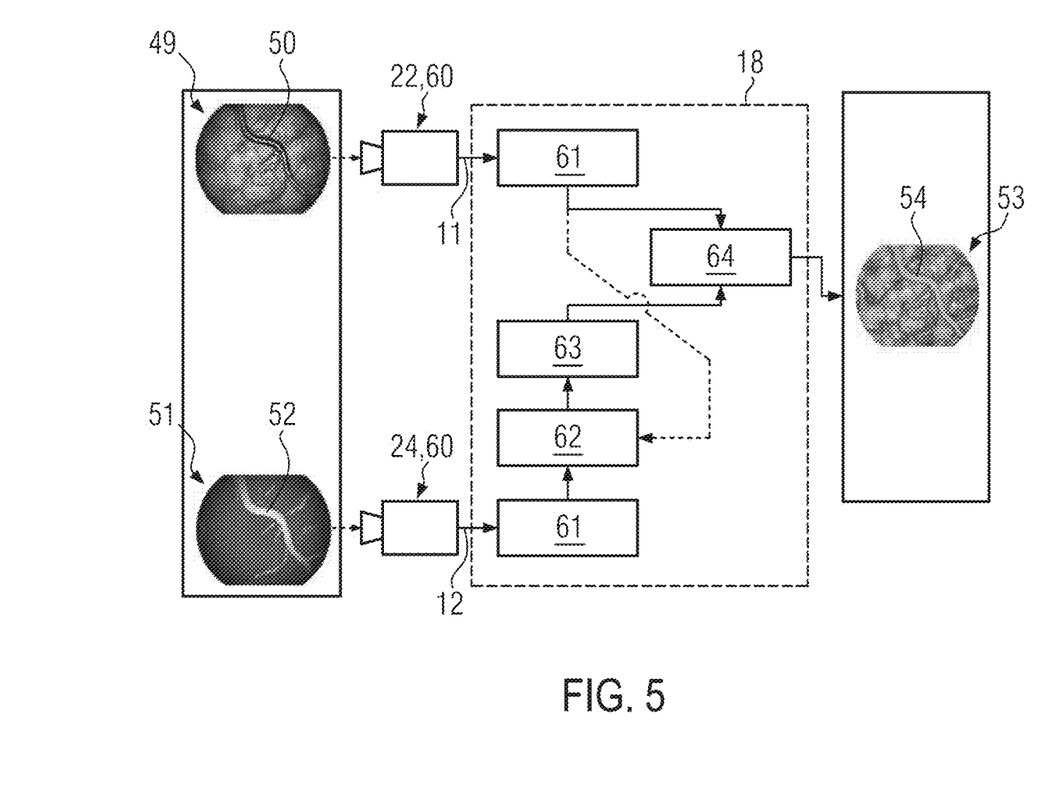
FIG. 5 shows a schematic representation of the assignment of pseudocolor in an image.
Figure 6:
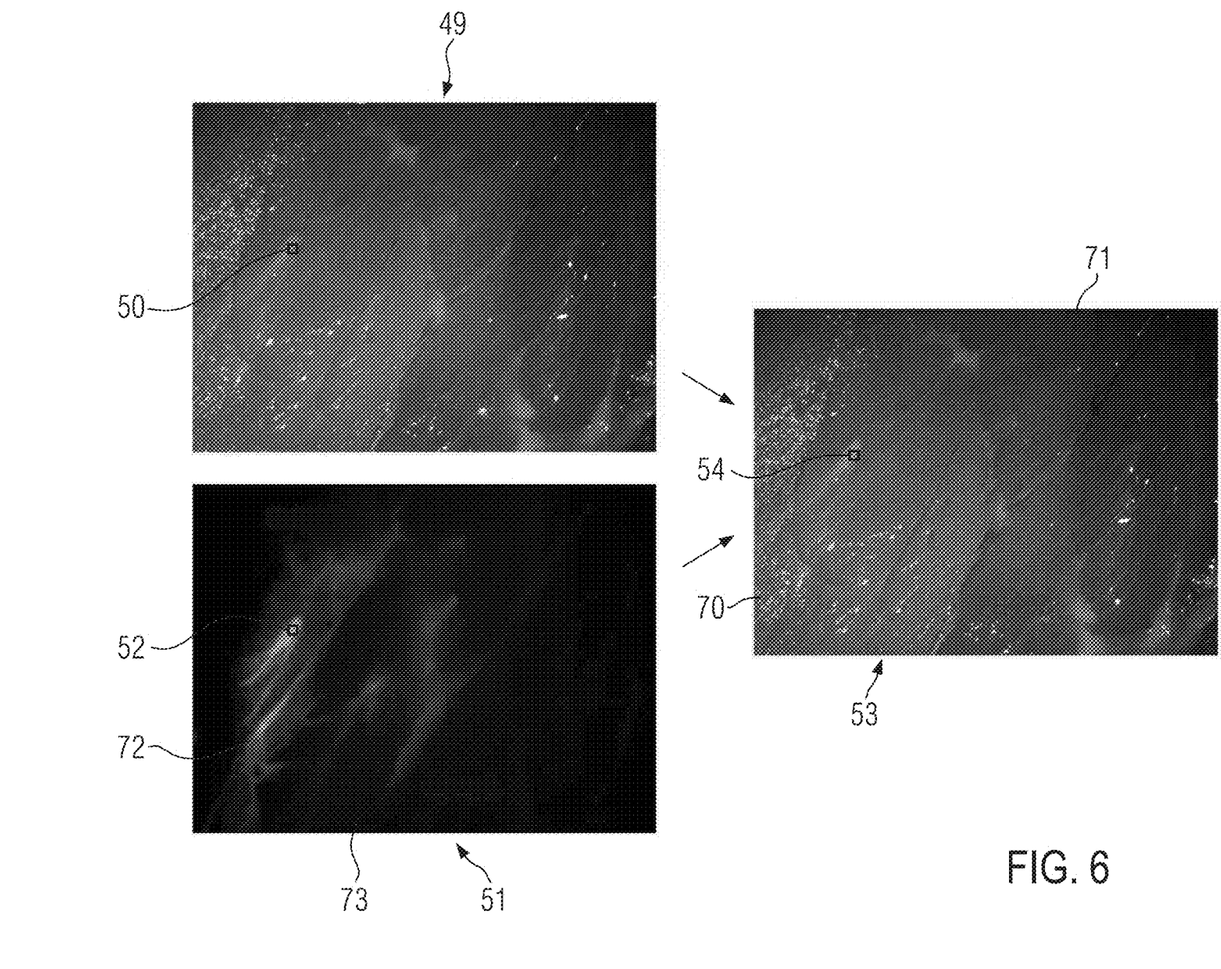
FIG. 6 shows a schematic representation of a pseudocolor image resulting from the use of more than one fluorophore.

FIG. 5 shows the generation of a pseudocolor image 53 containing two pseudocolors 70, 71. The two pseudocolors result from the use of two fluorofores in the object 2 which emit light at two different emission bands and thus have two different fluorescent colors 72, 72. In such a case, linear interpolation takes place after a pseudocolor 70, 71 has been assigned to a second input pixel 52 in the fluorescent-light image 51 based on the fluorescent color 72, 73 of the second input pixel 52. After this assignment, the linear interpolation in color space takes place between the pseudocolor assigned to the specific pixel 50, 52, 54 and the color of the first input pixel 50 as explained above.

Although the invention has been described above with reference to a microscope, it can be applied also to an endoscope, the only difference being that the optical subsystem 8 comprises fiber optics in the case of the endoscope as compared to a microscope 1.

REFERENCE NUMERALS 1 microscope
2 object
3 lighting subsystem
4 light source
5 light from lighting subsystem
6 fluorophore
7 illumination filter
8 reflected or emitted light from object
9 optical subsystem
10 imaging subsystem
11 visible image data
12 fluorescence image data
13 beam splitter
14 visible light
15 NIR light
16 visible-light imaging assembly
17 fluorescent-light imaging assembly
18 image processing unit
19 output data of image processing unit
20 visible observation filter
21 field of view
22 visible-light camera
23 fluorescence observation filter
24 fluorescent-light camera
25 data interface of fluorescent imaging subsystem
26 control signal
27 control and processing subsystem
30 controller unit
31 first input section
32 second input section
33 output section
35 documentation subsystem
36 monitoring subsystem
37 eyepiece display
38 microscope monitor
39 display interface
41 homogenization module
42 homogenization filter
43 calibration object for obtaining homogenization filter
44 spatial profile
45 spatial adjustment module
46 gamma correction module
47 threshold adjustment module
48 pseudocolor image generator
49 visible-light image
50 first input pixel
51 fluorescent-light image
52 second input pixel
53 pseudocolor image
54 output pixel
60 first step
61 second step
62 third step
63 fourth step
64 fifth step
70 first pseudocolor
71 second pseudocolor
72 first fluorescence color
73 second fluorescence color

What is claimed is:

1. A medical inspection apparatus comprising an image processing unit, the image processing unit comprising a first input section configured to receive visible image data representing a visible-light image of an object, a second input section configured to receive fluorescence image data representing a fluorescent-light image of the object, and an output section configured to output pseudocolor image data representing a pseudocolor image of the object, wherein the image processing unit is adapted to compute a color of an output pixel in the pseudocolor image from at least one pseudocolor, a color of a first input pixel in the visible-light image and an intensity of a second input pixel in the fluorescence-light image, wherein the color of the output pixel in a color space is located linearly between the color of the first input pixel and the at least one pseudocolor, and the distance in the color space between the color of the output pixel and the color of the first input pixel is proportionate to a relative intensity factor defined by the intensity of the second input pixel divided by a maximum expected fluorescence intensity of the second input pixel.

2. The medical inspection apparatus according to claim 1, wherein the fluorescent-light image contains at least two different fluorescent emission colors and wherein the image processing unit is configured to assign a different pseudocolor to each of the different fluorescent emission colors.

3. The medical inspection apparatus according to claim 1, wherein the image processing unit comprises a homogenization module, the homogenization module being configured to compensate at least one of vignetting and inhomogeneous illumination in at least one of the visible-light image and the fluorescent-light image.

4. The medical inspection apparatus according to claim 3, wherein the homogenization module comprises different homogenization filters for the visible-light image and data and for the fluorescent-light image.

5. The medical inspection apparatus according to claim 1, wherein the image processing unit comprises a threshold adjustment module configured to blank the second input pixel in the fluorescent-light image if the second input pixel has an intensity below a threshold value.

6. The medical inspection apparatus according to claim 1, wherein the processing unit comprises a spatial adjustment module, the spatial adjustment module being adapted to bring the visible-light image and the fluorescent-light image into congruence to each other.

7. The medical inspection apparatus according to claim 6, wherein the spatial adjustment module is adapted to at least one of crop, rotate, shift and stretch at least one of the visible-light image and the fluorescent-light image.

8. The medical inspection apparatus according to claim 1, wherein the medical inspection apparatus is a microscope.

9. The medical inspection apparatus according to claim 1, wherein the medical inspection apparatus is an endoscope.

10. A medical inspection method, comprising the steps of:
acquiring visible image data representing a visible-light image of an object;
acquiring fluorescence image data representing a fluorescent-light image of the object; and
combining the visible image data, the fluorescent light data and at least one pseudocolor to obtain pseudocolor image data representing a pseudocolor image, wherein a color of an output pixel in the pseudocolor image depends on the at least one pseudocolor, a color of a first input pixel in the visible-light image, and an intensity of a second input pixel in the fluorescent-light image;
wherein the color of the output pixel in a color space is located linearly between the color of the first input pixel and the at least one pseudocolor, and the distance in the color space between the color of the output pixel and the color of the first input pixel is proportionate to a relative intensity factor defined by the intensity of the second input pixel divided by a maximum expected fluorescence intensity of the second input pixel.

11. The medical inspection method according to claim 10, further comprising the step of assigning different pseudocolors to different fluorescent colors in the fluorescent-light image.

12. The medical inspection method according to claim 10, further comprising the step of bringing the visible-light image and the fluorescent-light image into congruence with each other before combining the visible-light image and the fluorescent-light image to obtain the pseudocolor image.

13. The medical inspection method according to claim 12, wherein at least one of the visible-light image and the fluorescent-light image is at least one of cropped, shifted, stretched and rotated for bringing the visible-light image and the fluorescent-light image into congruence with each other.

14. The medical inspection method according to claim 10, wherein the second input pixel is blanked in the fluorescent-light image if the intensity of the second input pixel is below a threshold.

15. The medical inspection method according to claim 10, wherein the medical inspection method is a microscopy method.

16. The medical inspection method according to claim 10, wherein the medical inspection method is an endoscopy method.

17. A non-transitory computer readable medium storing a program causing a medical inspection apparatus to execute a medical inspection method comprising the steps of:
acquiring visible image data representing a visible-light image of an object;
acquiring fluorescence image data representing a fluorescent-light image of the object; and
combining the visible image data, the fluorescent light data and at least one pseudocolor to obtain pseudocolor image data representing a pseudocolor image, wherein a color of an output pixel in the pseudocolor image depends on the at least one pseudocolor, a color of a first input pixel in the visible-light image, and an intensity of a second input pixel in the fluorescent-light image;
wherein the color of the output pixel in a color space is located linearly between the color of the first input pixel and the at least one pseudocolor, and the distance in the color space between the color of the output pixel and the color of the first input pixel is proportionate to a relative intensity factor defined by the intensity of the second input pixel divided by a maximum expected fluorescence intensity of the second input pixel.

* * * * *